United States Patent
Dews et al.

(10) Patent No.: US 7,189,261 B2
(45) Date of Patent: Mar. 13, 2007

(54) MODULAR HUMERAL PROSTHESIS AND METHOD

(75) Inventors: Paul M. Dews, Sherwood Park (CA); Dean Hughes, Cordova, TN (US); Abraham Salehi, Bartlett, TN (US); Jeff Sprague, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/754,273

(22) Filed: Jan. 9, 2004

(65) Prior Publication Data
US 2004/0143335 A1 Jul. 22, 2004

Related U.S. Application Data

(63) Continuation of application No. 09/800,367, filed on Mar. 6, 2001, now abandoned, which is a continuation of application No. 09/054,709, filed on Apr. 3, 1998, now Pat. No. 6,197,063.

(51) Int. Cl.
*A61F 2/40* (2006.01)
*A61F 2/30* (2006.01)

(52) U.S. Cl. .................................. 623/19.14

(58) Field of Classification Search ............ 623/19.11, 623/19.13, 10.12, 19.14, 22.4, 22.42, 22.44, 623/22.45, 22.46
See application file for complete search history.

(56) References Cited

U.S. PATENT DOCUMENTS

| | | | |
|---|---|---|---|
| 3,694,820 A | 10/1972 | Scales et al. |
| 3,803,641 A | 4/1974 | Golyakhovsky |
| 3,916,451 A | 11/1975 | Buechel et al. |
| 3,978,528 A | 9/1976 | Crep |
| 4,003,095 A | 1/1977 | Gristina |
| 4,040,131 A | 8/1977 | Gristina |
| 4,045,825 A | 9/1977 | Stroot |

(Continued)

FOREIGN PATENT DOCUMENTS

DE 29 32 744 8/1979

(Continued)

OTHER PUBLICATIONS

U.S. Appl. No. 60/201,503, filed May 3, 2000, Hartdegen.

(Continued)

*Primary Examiner*—Pedro Philogene
(74) *Attorney, Agent, or Firm*—Kilpatrick Stockton LLP

(57) ABSTRACT

A modular humeral prosthesis for replacement of the humeral head of a humerus. The prosthesis generally comprises a stem to be fitted to a resected humerus; a head sized and configured to approximate the humeral head; and an intermediate connecting member for connecting the stem to the head. The intermediate connecting member provides a desired angle of inclination or offset between stem and head. The head may be a traditional humeral head, or it may be an eccentric humeral head, with its mating portion being offset. The head may also comprise a groove or milled trench at least partially surrounding or otherwise defining mating portion. Also disclosed is a modular humeral prosthesis kit comprising a variety of different intermediate connecting members that may be selected to tit the prosthesis to the patient, and a method of replacing a humeral head in a patient.

17 Claims, 7 Drawing Sheets

U.S. PATENT DOCUMENTS

| | | | |
|---|---|---|---|
| 4,106,130 | A | 8/1978 | Scales |
| 4,135,517 | A | 1/1979 | Reale |
| 4,179,758 | A | 12/1979 | Gristina |
| 4,206,517 | A | 6/1980 | Pappas et al. |
| 4,219,893 | A | 9/1980 | Noiles |
| 4,279,041 | A | 7/1981 | Buchholz |
| 4,301,553 | A | 11/1981 | Noiles |
| 4,352,212 | A | 10/1982 | Greene et al. |
| 4,538,305 | A | 9/1985 | Engelbrecht et al. |
| 4,549,319 | A | 10/1985 | Meyer |
| 4,608,053 | A | 8/1986 | Keller |
| 4,634,444 | A | 1/1987 | Noiles |
| 4,650,489 | A | 3/1987 | Thompson |
| 4,676,797 | A | 6/1987 | Anapliotis et al. |
| 4,693,723 | A | 9/1987 | Gabard |
| 4,822,370 | A * | 4/1989 | Schelhas ............... 623/22.46 |
| 4,865,605 | A | 9/1989 | Dines et al. |
| 4,892,546 | A | 1/1990 | Kotz et al. |
| 4,908,032 | A | 3/1990 | Keller |
| 4,911,719 | A | 3/1990 | Merle |
| 4,919,669 | A | 4/1990 | Lannelongue |
| 4,919,670 | A | 4/1990 | Dale et al. |
| 4,921,500 | A | 5/1990 | Averill et al. |
| 4,938,773 | A | 7/1990 | Strand |
| 4,957,510 | A | 9/1990 | Cremascoli |
| 4,963,155 | A | 10/1990 | Lazzeri et al. |
| 4,986,833 | A | 1/1991 | Worland |
| 5,002,578 | A | 3/1991 | Luman |
| 5,002,581 | A | 3/1991 | Paxson et al. |
| 5,015,257 | A | 5/1991 | Crowninshield et al. |
| 5,108,452 | A | 4/1992 | DeMane et al. |
| 5,156,624 | A | 10/1992 | Barnes |
| 5,201,882 | A | 4/1993 | Paxson |
| 5,282,865 | A | 2/1994 | Dong |
| 5,314,479 | A | 5/1994 | Rockwood, Jr. et al. |
| 5,358,526 | A * | 10/1994 | Tornier ................. 623/19.14 |
| 5,462,563 | A | 10/1995 | Shearer et al. |
| 5,489,309 | A | 2/1996 | Lackey et al. |
| 5,507,814 | A | 4/1996 | Gilbert et al. |
| 5,507,817 | A | 4/1996 | Craig et al. |
| 5,507,818 | A | 4/1996 | McLaughlin |
| 5,549,682 | A | 8/1996 | Roy |
| 5,549,703 | A | 8/1996 | Daigle et al. |
| 5,580,352 | A | 12/1996 | Sekel |
| 5,658,340 | A | 8/1997 | Müller et al. |
| 5,702,457 | A | 12/1997 | Walch et al. |
| 5,702,486 | A * | 12/1997 | Craig et al. .............. 623/19.14 |
| 5,728,161 | A | 3/1998 | Camino et al. |
| 5,800,556 | A | 9/1998 | Sanders et al. |
| 5,902,340 | A | 5/1999 | White et al. |
| 5,906,644 | A | 5/1999 | Powell |
| 5,910,171 | A * | 6/1999 | Kummer et al. .......... 623/18.11 |
| 5,944,758 | A | 8/1999 | Manset et al. |
| 6,129,764 | A | 10/2000 | Servidio |
| 6,171,341 | B1 | 1/2001 | Boileau et al. |
| 6,197,063 | B1 | 3/2001 | Dews |
| 6,228,120 | B1 | 5/2001 | Leonard et al. |
| 6,673,114 | B2 | 1/2004 | Hartdegen et al. |
| 2001/0053935 | A1 | 12/2001 | Hartegen et al. |
| 2002/0016634 | A1 | 2/2002 | Maroney et al. |
| 2002/0095215 | A1 | 7/2002 | Camino et al. |
| 2003/0074079 | A1 | 4/2003 | McTighe et al. |
| 2003/0074080 | A1 | 4/2003 | Murray |

FOREIGN PATENT DOCUMENTS

| | | |
|---|---|---|
| DE | 44 01 952 C1 | 1/1994 |
| DE | 4320086 | 12/1994 |
| DE | 195 09 037 C1 | 9/1996 |
| EP | 0 041 591 A1 | 1/1981 |
| EP | 0 099 167 | 1/1984 |
| EP | 0 127 503 A1 | 12/1984 |
| EP | 0 201 407 A1 | 11/1986 |
| EP | 0 201 407 B1 | 11/1986 |
| EP | 0 216 489 A1 | 4/1987 |
| EP | 0 278 807 A3 | 8/1988 |
| EP | 0 299 889 A3 | 1/1989 |
| EP | 0 299 889 B1 | 1/1989 |
| EP | 0 485 311 A1 | 5/1992 |
| EP | 0 599 429 A2 | 6/1994 |
| EP | 0 639 359 A1 | 2/1995 |
| EP | 0 664 108 A2 | 7/1995 |
| EP | 0 679 375 A1 | 11/1995 |
| EP | 0 712 617 A1 | 5/1996 |
| FR | 2 617 706 | 1/1989 |
| FR | 2 647 670 | 12/1990 |
| FR | 2 652 498 | 4/1991 |
| FR | 2 664 809 | 1/1992 |
| FR | 2697996 | 5/1994 |
| FR | 2 721 200 | 12/1995 |
| FR | 2721200 * | 12/1995 ............ 623/19.14 |
| GB | 1 438 950 | 6/1976 |
| GB | 1 548 750 | 7/1979 |
| GB | 2 223 172 | 4/1990 |
| GB | 1 292 561 | 10/1992 |
| WO | WO 94/15551 | 7/1994 |
| WO | WO 95/22302 | 8/1995 |
| WO | WO 96/17553 | 6/1996 |
| WO | WO 96/38104 | 12/1996 |
| WO | WO 96/41597 | 12/1996 |
| WO | WO 98/15241 | 4/1998 |
| WO | WO 00/15154 | 3/2000 |
| WO | WO 00/41653 | 7/2000 |

OTHER PUBLICATIONS

"Surgical Protocol Modular Shoulder" brochure, 3M Health Care Ltd. 1994.

"Product Specification" brochure, 3M Health Care Ltd. 1994.

"3M Modular Shoulder Ideas in Motion" brochure, 3M Health Care Ltd. 1994.

"Neer II Total Shoulder System" brochure, 3M Health Care Ltd. 1989.

Biomet, Inc.—Shoulder Systems, http://www.biomet/com/product/shoulder.html (© 1997), plus pages on Bio-Modular™, Bi-Angular™, Bi-Angular/Bi-Polar™, Integrated Shoulder System™, and Proximal Humeral Replacement™, DePuy, Product Information: Global™ Total Shoulder System, http://www.depuy.com/products/global.htm (last updated Mar. 13, 1998.).

Homedica: MRS, http://www.howmedica./mrs/shoulder.htm, http:/www.howmedica.com/mrs/shoulder1.htm, http://www.howmedica.com/mrs/shoulder2.htm, http://www.howmedica.com/mrs/shoulder3.htm (printed May 29, 1998).

Daniel E. Williamson, M.S., Design Considerations in Total Shoulder Arthroplasty Relating to Long-Term Glenohumeral Stability (© 1994 Biomet, Inc.).

* cited by examiner

MODULAR HUMERAL PROSTHESIS AND METHOD

This application is a continuation application of U.S. Ser. No. 09/800,367 filed Mar. 6. 2001 now abandoned entitled "Modular Humeral Prosthesis And Method" which is a continuation in part of U.S. Ser. No. 09/054,709 filed Apr. 3, 1998 now U.S. Pat. No. 6,197,063 entitled "Modular Huineral Prosthesis and Method."

BACKGROUND OF THE INVENTION

During the procedure of a shoulder replacement operation, at least a portion of the proximal section of the humeral shaft will be replaced by a metal prosthesis. This prosthesis will generally consist of two parts: a stem that is mounted into the medullary canal of the humerus, and a head component connected in some manner to the stem. The head component replaces the bearing surfaces of the humerus and articulates with the surface of the scapula to allow the movement of the shoulder.

Modular humeral prostheses are known. The stem and head component may be supplied in "modular" form, that is, as separate connectable components. Different stem sizes and head sizes in a modular implant design provide the surgeon with some degree of inter-operative flexibility, which facilitates reconstruction of the original anatomy of the patient.

With a range of stem sizes and a range of head sizes available, the surgeon can choose a particular combination to suit the anatomy of each individual patient without having to stock a large inventory of "integral" or "unitary" humeral prostheses. As used herein, "integral" and "unitary" mean formed in one continuous piece in contrast to the separate connectable components of a modular prosthesis. For example, one patient might require a relatively small head and a relatively long stem. With a unitary prosthesis a wide range of stem lengths would be required for each head size whereas with a modular arrangement a particular head can be used with a range of stem sizes and visa versa.

Additional variations arise also as a result of individual patients requiring differing angles of inclination of the head relative to the stem and differing offsets between the axis of the head and the axis of the stem. Thus, in one patient the offset may be posterior and in another anterior.

Various shoulder prostheses are disclosed in European Patent Publication No. EP-A 0 679 375 to Odella dated Sep. 2, 1998; EP-A 0 712 617 to Walch, et al. dated Sep. 29, 1999; French Patent No. FR-A 2 664 809 to Travers dated Dec. 26, 1997; U.S. Pat. No. 3,694,820 to Scales, et al. dated Oct. 3, 1972; U.S. Pat. No. 3,803,641 to Golyakhousky dated Apr. 16, 1974; U.S. Pat No. 4,045,825 to Stroot dated Sep. 6, 1977; U.S. Pat No. 4,106,130 to Scales dated Aug. 15, 1978; U.S. Pat. No. 4,179,758 to Gristina dated Dec. 25, 1979; U.S. Pat. No. 4,865,605 to Dines, et al. dated Sep. 12, 1989; U.S. Pat. No. 4,919,670 to Dale, et al. dated Apr. 24, 1990; U.S. Pat. No. 5,358,526 to Tornier dated Oct. 25, 1994; U.S. Pat. 5,549,682 to Roy dated Aug. 27, 1996; U.S. Pat. No. 5,462,563 to Shearer, et al. dated Oct. 31, 1995 and U.S. Pat. No. 5,702,457 to Walch, et al. dated Dec. 30, 1997; and PCT International Patent Publication No. WO 96/17553 to McDaniel, et al. dated Jun. 13, 1996, which are all incorporated herein by this reference.

SUMMARY OF THE INVENTION

This invention provides a modular prosthesis in which a humeral head, chosen to suit a patient, is attached to a stem chosen to suit the resected humerus of the patient by means of an intermediate connecting member. The prosthesis can accommodate a wide range of variation in, for instance offset and/or angle, in a relatively inexpensive and efficient manner, by accommodating the variations in the intermediate connecting member rather than in the head.

Additionally, prostheses according to the present invention can include a traditional modular humeral head as well as an eccentric modular humeral head. The eccentric head features a portion that is offset from the radial center of the humeral head that cooperates with the intermediate connecting member. This eccentric head embodiment works in conjunction with the intermediate connecting member, allowing the surgeon even further variations and options during the surgery.

The modular humeral prosthesis generally comprises a stem adapted to be fitted to a resected humerus, a head adapted to approximate the size and shape of a humeral head, and an intermediate connecting member for connecting the stem to the head. The intermediate connecting member includes two connecting surfaces or other engagement structure. The first connecting surface is adapted to cooperate with a structure forming part of the stem in order to mount the intermediate connecting member to the stem. The second connecting surface is adapted to cooperate with a structure forming part of the head in order to mount the head to the intermediate connecting member. Preferably, the second connecting surface is partially nested with the first connecting surface. The connecting surfaces are preferably surfaces of rotation having axes of rotation, so that they are provided with a full range of rotational motion.

For example, the first connecting surface or engagement means for mounting the intermediate connecting member on the stem, may have an axis about which the intermediate connecting member can be rotated through 360° relative to the stem and thereafter secured at a selected relative orientation. The second connecting surface or engagement means for mounting the head on the intermediate connecting member may have an axis about which the head can be rotated through 360° relative to the intermediate connecting member and thereafter secured at a selected relative rotation.

In one embodiment, the axes of rotation of the first and second connecting surfaces are not coincident or collinear, allowing the head to be given a desired offset relative to the stem.

In another embodiment, the axis of rotation of the first and second connecting surfaces are not parallel, allowing a desired inclination of the head relative to the stem. Furthermore, the first and second connecting surfaces of the intermediate connecting member may be positioned relative to one another to provide a desired separation between the head and the stem. Preferably, the separation or "neck length" between the head and the stem is no greater than 5 mm, but this may vary depending upon surgeon preferences.

In a further embodiment, the connecting surfaces provide both an offset and an angle of inclination, so that in use, the head is offset and angled relative to the stem.

Also, the first and second connecting surfaces may each comprise a male or female portion, and the head and stem are provided with corresponding mating portions. The male and/or female portions preferably each have a substantially circular cross-sections, and a substantially self-locking tapered configuration (i.e., a Morse taper). A "Morse taper" is taper that forms an angle providing a self-locking function.

It is possible for a bore to be provided through the first and second connecting surfaces that extends through the intermediate connecting member, the prosthesis further comprising a fastener inserted through the bore to engage the stem further to secure the intermediate connecting member to the stem.

In another aspect of the invention, a modular humeral prosthesis kit is provided for replacement of the humeral head of a humerus. The kit generally comprises a stem adapted to be fitted to a resected humerus, a head sized and configured to approximate the humeral head, and a plurality of intermediate connecting members of which one may be selected to connect the stem to the head. Each intermediate connecting member includes a first connecting surface for mounting the intermediate connecting member on the stem, and a second connecting surface for mounting the head on the intermediate connecting member. The plurality of the intermediate connecting members of the kit include:
  A. at least one intermediate connecting member in which the first and second connecting surfaces share an axis of rotation;
  B. at least one intermediate connecting member in which the first and second connecting surfaces are offset from each other; and
  C. at least one intermediate connecting member in which the first and second connecting surfaces are inclined at an angle relative to each other.

In another embodiment, the plurality of intermediate connecting members of the kit include:
  A. at least one intermediate connecting member in which the first and second connecting surfaces have generally parallel and coincident central axes;
  B. at least one intermediate connecting member in which the first and second connecting surfaces have generally parallel but not coincident central axes;
  C. at least one intermediate connecting member in which the first and second connecting surfaces have an angle of inclination between one another that is different than the angle of inclination between the first and second connecting surfaces of another intermediate connecting member of the kit; and
  D. at least one intermediate connecting member in which the first and second connecting surfaces are separated by a different neck length than the neck length separating the first and second connecting surfaces of another intermediate connecting member of the kit.

The specifications for the plurality of intermediate connecting members described above may be met by combining features in some of the intermediate connecting member of the kit. For example, two intermediate connecting members may have different neck lengths, angles of inclination and offsets or zero offset.

Preferably, the first connecting surface of each intermediate connecting member has an axis about which the intermediate connecting member can be rotated through 360° relative to the stem and thereafter secured at a selected relative orientation, and the second connecting surface of each intermediate connecting member has an axis about which the head can be rotated through 360° relative to the intermediate connecting member and thereafter secured at a selected relative rotation.

Preferably, the first connecting surface of each intermediate connecting member comprises a female portion, and the stem is provided with a corresponding mating male portion, and the second connecting surface comprises a male portion having the first connecting surface nested therein, and the head is provided with a corresponding mating portion, such as a female cavity. Most preferably, the male and female portions each have a substantially circular cross-section, and a substantially self-locking tapered configuration (i.e., a Morse taper).

In a further embodiment, the surgeon is provided with the option of using a traditional humeral head, having its corresponding mating portion at the approximate center of the radius of the humeral head, or using an eccentric humeral head, having its corresponding mating portion offset from the center of the radius of the humeral head.

According to other aspects of the invention, methods of replacing a humeral head in a patient generally comprise:
  (a) Resecting the proximal end of the humerus to remove the head and expose the medullary canal of the humerus;
  (b) Inserting the stem of a prosthesis into the medullary canal of the resected humerus, the prosthesis being modular and comprising:
    (i) a stem;
    (ii) an eccentric humeral head; and
    (iii) one of a plurality of intermediate connecting members for connecting the stem to the head; each intermediate connecting member including:
      a first, female, connecting surface forming a cavity that is adapted to receive a structure that protrudes from the stem in order to mount the intermediate connecting member to the stem; and
      a second, male, connecting surface adapted to be received in a cavity in the head in order to mount the head to the intermediate connecting member,
      the second connecting surface at least partially nested with the first connecting surface;
      the plurality of intermediate connecting members including at least some members having different angles of inclination between their first and second connectors;
  (c) selecting a particular intermediate connecting member to provide a desired angle of inclination of the head relative to the humerus; and
  (d) mounting and locking the intermediate connecting member to the stem, and mounting and locking the intermediate connecting member to the head, the mounting and locking of the intermediate connecting member to the stem and head imparting any desired angle of inclination of the head relative to the humerus.

The plurality of intermediate connecting members may include intermediate connecting members having different neck lengths separating the first and second connecting surfaces, and the methods further comprise selecting an intermediate connecting member to provide a desired separation between the head and the stem.

The surgeon will still need her traditional range of head sizes and stem sizes and lengths. However, the surgeon does not need additional heads or stems to provide a particular orientation of the head or a particular offset for the head, although the surgeon may prefer to use the eccentric head option described herein. Thus, while a range of intermediate connecting members are required to be available to choose particular offsets and orientations, those intermediate connecting members are relatively inexpensive compared with the normally considerable cost of the highly sophisticated head component.

Also, it is an advantage of the invention that the surgeon can choose quite independently of one another the three component parts. Thus, the surgeon does not have to be concerned with questions of offset and orientation when selecting the right head size, except to the extent that she prefers to use an eccentric head. The same is true as regards the stem: the surgeon can choose the correct stem to fit the medullary canal in the humerus and so give a long lasting and secure joint between the stem and the bone. Having selected these components, the surgeon can, quite independently, decide on the particular offset and/or orientation of the head relative to the stem and select an intermediate connecting member accordingly. The surgeon is, therefore, able to match the modular prosthesis used to the original anatomy of a particular patient. Because a shoulder joint is enclosed and surrounded by soft tissue, it is preferable (but not necessary) that the spacing between the end of the stem and the head be kept to a minimum, e.g. no greater than 5 mm.

The typical surgical procedure for the implantation of a humeral prosthesis includes the determination of the longitudinal axis of the humerus, drilling a hole in the proximal margin between the head and the tuberosity in line with this, then inserting a starter reamer or broach, and developing a bore hole along the longitudinal axis of the humerus. Next, this bore hole can be enlarged by using progressively larger reamers or broaches, until the surgeon determines that the reamer or broach being used is the largest possible fit into the available cavity without the excessive removal of cortical bone. Then, the head is accurately removed from the proximal portion of the humerus, and a flat angled face is prepared on the proximal portion of the humerus, usually along the line of the anatomical neck, by means of a resection guide.

The cavity thus prepared, the trial stem can be introduced. At this stage, the surgeon is able to determine the amount of anteversion that is appropriate for the patient. Once in place, the head measurement instrument can be attached, and the trial head attached to this. This head measurement instrument allows the accurate placement of the head in a number of different positions so that the surgeon can assess which position best suits the anatomy of the patient. Once determined, the surgeon can, in one aspect of the invention, read off the specific orientation of the head from a scales or indicia on the instrument; this determines which intermediate connecting member is to be used with the definitive implant.

It is not possible to provide an infinite number of intermediate connecting members so as to cover every possibility of adjustment. In practical terms, therefore, one provides a range of intermediate connecting members in incremental sizes to provide a range of discrete adjustments in just the same way that a discrete number of heads and stems are provided. However, because the connecting surfaces allow the relative rotation of the components, one can with a single intermediate connecting member choose an amount of offset and that amount can be positioned on a locus throughout 360°. The same, of course, is true as regards the inclination of the axis of the head relative to the stem.

Another reason that having a range of intermediate connecting members is helpful to the surgeon is because it allows the surgeon to replace the intermediate connecting member without removing the entire stem. For example, in a revision surgery, the surgeon may want to change the angulation or the offset of the head member with respect to the stem without removing the stem. Providing the surgeon with an intermediate connecting member allows the surgeon to use the intermediate connecting member to angulate the head with respect to the stem or offset the head with respect to the stem without requiring a whole new implant. The surgeon can use the intermediate connecting member to change inclination or offset so that the head will correspond appropriately to the stem.

In a preferred embodiment of the invention, the intermediate connecting member is available in a discrete number of sizes, each size providing an incremental increase in the separation between the two connecting surfaces. Thus, the surgeon is provided with a variety of parts from which to choose in order to approximate best the patient's original anatomy by selecting a part that will provide the closest approximation of the original separation between the humeral head and the humeral stem.

It is preferred that the second connecting surface be located at the center of the base of the humeral head. Thus, in this embodiment, the relative rotational placement of the head component has no effect in altering the angle of inclination of the head or the axial offset of the head in relation to the stem or even the separation between the head and the stem. If the surgeon desires that the humeral head itself should have an offset, she may use an eccentric head in conjunction with the intermediate connecting member. It is not essential that the second connecting surfaces be of circular cross-section although this is preferred. This provides the advantage that fewer of the expensive head components are required to achieve this range of variables. Naturally the head will have to be provided in a number of incrementally varying sizes to fit the needs of each individual patient's scapula or glenoid prosthesis. Additionally, in an alternate embodiment, there are also provided eccentric heads in a number of incrementally varying sizes. The portion of the connecting surface forming part of the intermediate connecting member can both be male or alternatively one can be male and the other female.

It is further preferable that the connecting surfaces will each be of a substantially cylindrical shape, whether male or female, and therefore allow the intermediate connecting member to be rotatable relative to the stem and the head rotatable relative to the intermediate connecting member before securement. To fix one part relative to the other the cylinders of the male and female portions are preferably of the Morse taper type. This fixing may be supplemented by a screw or other fastener fixation. In order to satisfy the criterion for strength, it is desirable that the intermediate connecting, member be formed in one piece. It is, however, within the scope of this invention that the intermediate connecting member be formed from a plurality of pieces.

BRIEF DESCRIPTION OF THE DRAWINGS

Embodiments of the invention will now be described by way of example and with reference to the accompanying schematic drawings, in which.

DETAILED DESCRIPTION OF PREFERRED EMBODIMENTS

Figures 1, 2:
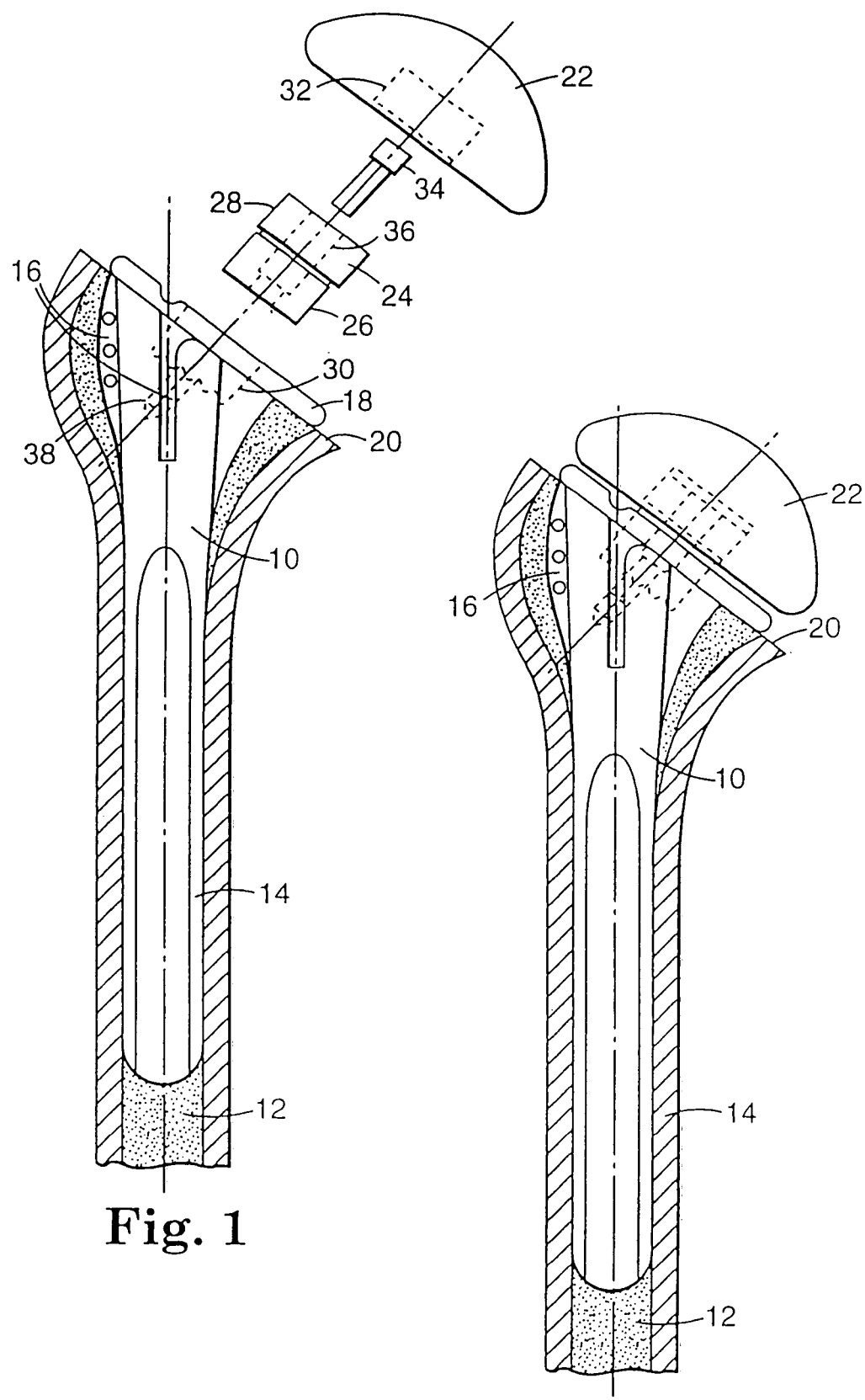
FIG. 1 is an exploded side elevation of a modular humeral prosthesis according to the invention.
FIG. 2 is the assembled prosthesis of FIG. 1.

The stem 10 shown in FIG. 1 is available in a number of different sizes to match the size to which the medullary canal 12 has been reamed or broached. The shaft of the stem 14 is designed to contact the previously reamed or broached medullary canal 12 and extend into the remaining humerus to prevent any undesired movement of the stem 10.

The stem 10 may be prevented from rotating by the use of fins 16 located at the neck of the stem 10. These fins 16 are wedged into the proximal position of the humerus to prevent any undesired movement of the stem 10 and offer some additional support to the face 18 of the stem 10. The face 18 of the stem 10 fits onto the previously prepared face of the humerus 20, and is designed so that the angle of the face 18 is roughly equal to that of the anatomic neck of the humerus. Coassigned U.S. patent application Ser. No. 08/946,758, filed Oct. 8, 1997, and PCT International patent application No. US97/18207, filed Oct. 8, 1997, both by Michel Mansat et al disclose a shoulder prosthesis with fins, and are incorporated herein by reference.

The humeral head 22 is designed to articulate with the scapula or glenoid prosthesis (not shown). The head 22 replaces the articulating surface of the humerus and is largely hemispherical in shape. A variety of sizes of head 22 are provided to complement the patient's scapula or glenoid prosthesis. The articulating surface of the head 22 is highly polished to reduce friction, hence wear, on the scapula or glenoid prosthesis.

Based on proximal humeral morphology, the humeral head center of the preferred embodiment is generally medialized and offset posteriorly from the humeral canal. In fact, there is about a 3 mm posterior offset in an average individual. In order to provide optimal proximal humeral bone coverage, it is useful to provide the surgeon with the option of using an eccentric head 200, shown in FIG. 17.

As with a traditional humeral head, eccentric humeral head 200 is also designed to articulate with the scapula or glenoid process. However, instead of having a centered mating portion, head 200 according to the preferred embodiment has an eccentric mating portion 202. Eccentric mating portion 202 is not coaxial with the head, i.e., it is offset from the center of the humeral head articular radius. This eccentricity helps to align the proximal humeral stem with the glenoid, providing a shift in the normal anatomy.

Eccentric humeral head 200 is shown as having a female taper that is offset from the center of the humeral head articular radius. It should be understood, however, that mating portion 202 may be any connecting structure, such as a male mating portion, a tapered mating portion (whether or not male), and the like. The essence of the invention is that the humeral head itself displays eccentricity. This eccentricity may range from 1 mm to 5 mm. If eccentric head 200 is used in conjunction with an intermediate connecting member, it allows the surgeon to achieve more options to fit various patient geometries.

The variation in patient anatomy, inclination angle, retroversion, and posterior offset of the humeral head necessitate the need for a multitude of intra-operative adjustments. Eccentric head 200 allows the surgeon during surgery to adjust for inclination, retroversion, and/or eccentricity. During intra-operative trialing, which the surgeon performs in order to place the correct amount of tension on the soft tissue and supporting tendons, the proper humeral head size (height and diameter) is initially selected. The eccentric humeral head 200 enables the surgeon to adjust the humeral head prosthesis in order properly to position the humeral head in an optimum position with respect to the glenoid articular surface, as well as with respect to the tuberosity attachment site. The ability to adjust the eccentricity in the plane of the selected inclination angle along with the ability to adjust retroversion is a distinct advantage in achieving optimal joint balancing and increased range of motion.

For example, if the surgeon wishes to vary the inclination angle or provide an offset of the head with respect to the stem, use of an intermediate connecting member, described below, can help achieve this configuration. However, if the surgeon wishes to alter the retroversion angle of the center of the head with respect to the glenoid, the use of eccentric head 200 helps achieve this configuration. An eccentric head used in conjunction with an intermediate stem member allows the surgeon to vary inclination, retroversion, eccentricity and offset, providing the surgeon with an increased range of usability and possibilities to fit various patient features or irregularities.

Of course, eccentric head 200 may be employed with or without an intermediate connecting member. In other words, the eccentric head described herein may be used coupled directly to the humeral stem. It may also be used in conjunction with an intermediate connecting member that has an offset, that provides an angle, or a combination of both or neither. Additionally, eccentric head 200 may be used as an actual implant or as part of a trialing system or method. An exemplary trialing method is described in copending Provisional Application U.S. Ser. No. 60/201,503 to Hartdegen filed May 3, 2000, incorporated herein by reference.

Figure 17:
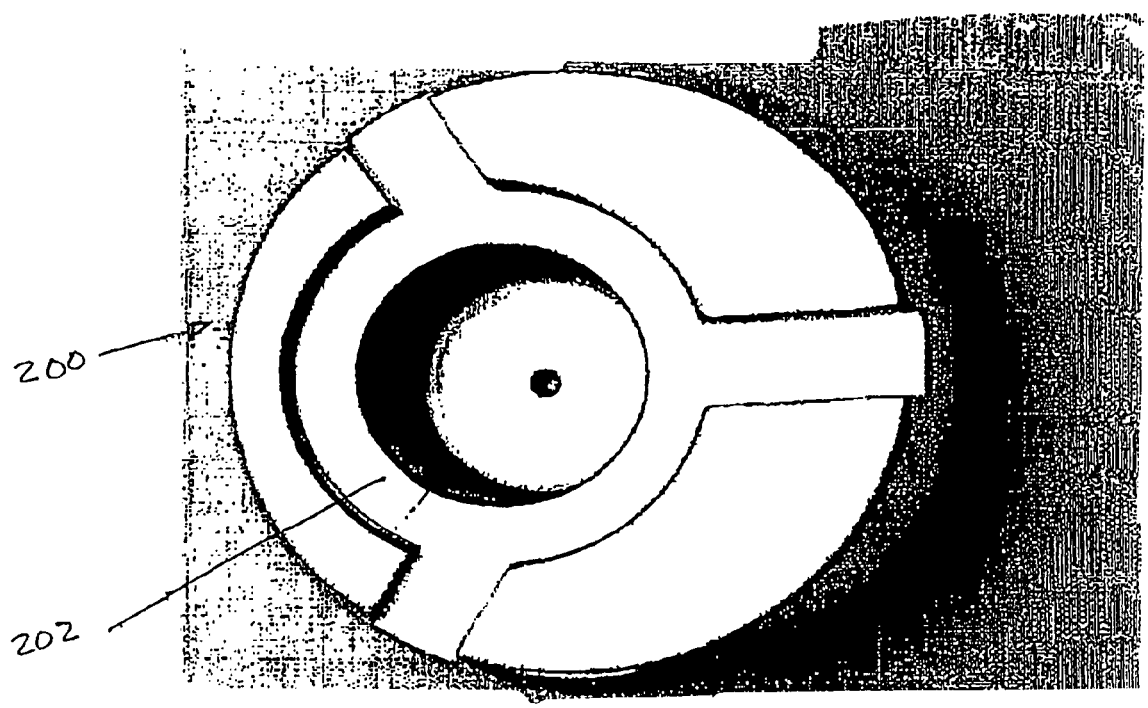
FIG. 17 is a bottom plan view of a preferred embodiment of an eccentric head according to the invention.
Figure 18:
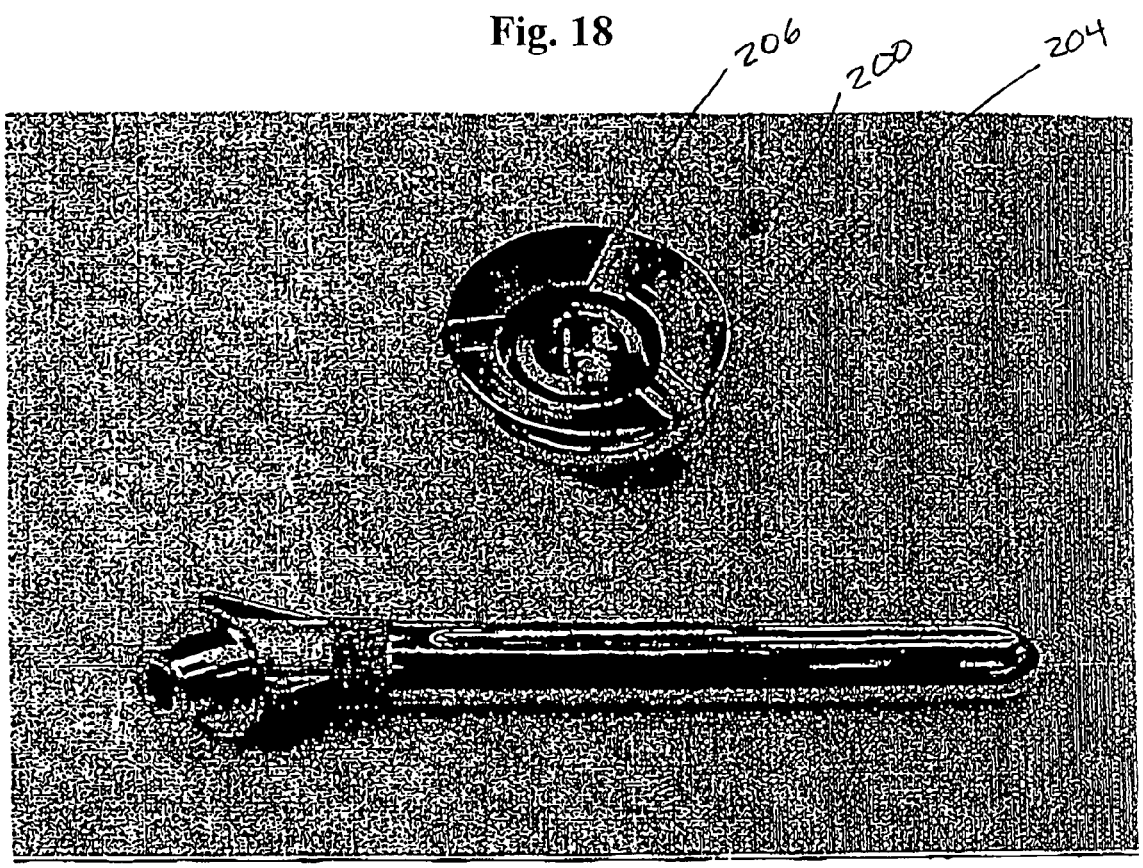
FIG. 18 is a bottom plan view of the eccentric head of FIG. 17, having a milled trench.

In a further embodiment, as shown in FIG. 18, eccentric head 200 has a female mating portion and trench 204 or groove defining mating portion 202. Trench 204 is any groove, indentation, or removed portion that may be milled, molded or otherwise formed. It is located circumferentially around and substantially surrounds or otherwise defines mating portion 202. Trench 204 may extend the entire circumference of the inside of the humeral head, or it may be divided by distraction slots 206 as shown in FIGS. 17 and 18.

Trench 204 preferably extends to the edge of the modular humeral head. Trench 204 may be any depth, but preferably extends to the bottom of the taper, approximately ten millimeters, though it is possible to provide a shallower trench 204. It is preferred that trench 204 extend to the depth at which the head and stem engage when in use. Put another way, trench 204 should extend to the depth where modular humeral head fully cooperates with the end of intermediate connecting member or stem when in use.

Providing a trench 204 on eccentric head 200 imparts a number of advantages. It provides increased distraction forces, so that when the surgeon impacts the head on the stem, the head provides superior locking forces with respect to the stem taper or intermediate connecting portion. It should be noted that trench 204 may achieve the described advantages if provided on either eccentric head 200 or on a traditional humeral head. It should also be noted that any head having a trench 204 may be used with or without an intermediate connecting member. For purposes of this document, reference to head 22 also includes a reference to eccentric head 200, a head with a trench 204 (whether traditional or eccentric), or both.

In use, it is believed that trench 204 allows the female taper to expand, creating hoop stress, which are tensile stresses along circumference of taper/lock interface. The increased tensile stresses help hold the two tapers together and thereby increase distraction forces between the two mating surfaces.

Without limitation to any theory, it is believed that the trench 204 allows taper to receive and seat further the portion with which it connects (whether it be the connecting surface of intermediate connecting member or the stem). As the taper expands, the portion with which it connects can seat even further and deeper into the taper, providing increased locking forces. To the contrary, a solid head not having trench 204 does not provide this benefit because there is no room for the taper to expand. Trench 204 on head 200 strengthens the attachment of the head to a corresponding component.

Currently, other device manufacturers offer only eccentric heads. However, consideration must be given to the locking device when the center line of the Morse tapers are not co-axial. The ability of the eccentric head to provide a substantial lock with respect to the stem taper or intermediate member has not been considered in current designs. This invention provides, in preferred embodiments, a superior locking means by the presence of a trench 204, which provides an increase in taper locking strength. The addition of the trench 204 provides the opportunity to provide up to at least 5 mm of eccentricity, an option that no other system currently provides.

Because of the increased distraction forces that are required to remove the head from the stem, eccentric head 200 is shown having distraction slots 206. Distraction slots 206 provide an opening, which allows the surgeon to use an osteotome or other instrument to apply a lever-type motion to more easily remove the head from the stem.

An intermediate connecting member 24 as shown in FIG. 1 has first and second male tapers 26 and 28 of the "Morse taper" type. Once pushed together two Morse taper parts tend to stay together. The first taper 26 is designed to connect with the stem 10 and the second taper 28 with the head 22. The tapers 26 and 28 are aligned in generally opposite directions for mating with a female taper 30 of the stem 10 and a female taper 32 of the head 22.

The first male taper 26 may also be held onto the female taper 30 of the stem 10 by means of a locking screw 34, which fits into a counter-bored hole 36 in the intermediate connecting member 24. The axis of this counter-bored hole 36 is aligned along the central axis of the taper 26 and the screw fits into this counter-bored hole 36 and locates into a threaded hole 38 in the stem 10.

The male tapers 26, 28 of the intermediate connecting member 24 can be securely connected with the respective female tapers 30, 32 of the stem 10 and head 22, which are also of the Morse taper type and match the tapers of the intermediate connecting member 24 by applying an external force, to form an interference fit between the mating tapers 24 and 30, and 26 and 32, as shown in FIG. 2.

The first and second male tapers 26 and 28 constitute one embodiment of the first and second connecting surfaces of the intermediate connecting member 24. Alternatives include other connecting or mating parts that define the relative orientation and position of the head 22 and the intermediate connecting member 24 or the stem 10 and the intermediate connecting member 24. For example, the first and/or second male tapers 26 and 28 could be replaced by female tapers (not shown) and the female tapers 30 and 32 of the stem 10 and/or head 22 replaced by male tapers (not shown).

There can be a large variety in the shape, size and orientation of human humeral bones and therefore it is desirable to tailor the humeral prosthesis to suit each individual case. The various designs of intermediate connecting members of the present invention provide a considerable range of different head positions and orientations relative to the humeral stem that can be selected and connected interoperatively.

The position of the head 22 can be varied by using different intermediate connecting members 24 as are appropriate in each individual case. Various designs of intermediate connecting members 24a—a are illustrated in FIGS. 3 to 7.

In each of these cases the intermediate connecting member 24a–e has the same elements and is joined to the stem 10 and head 22 as described above.

Figure 3:
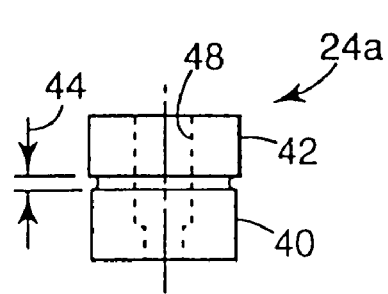
FIGS. 3–7 are various intermediate connecting members according to the invention.

One configuration of an intermediate connecting member 24a is illustrated in FIG. 3. In this configuration, the first male taper 40 and the second male taper 42 are axially aligned with minimum separation or "neck length" 44 between them. The design of this intermediate connecting member 24a matches the anatomical design of some patients' original humerus.

Figure 4:
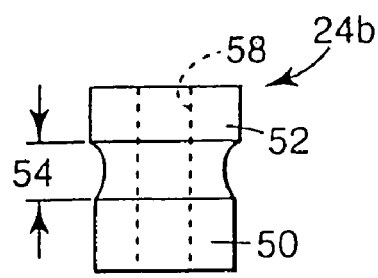

For other patients, a larger separation between the head 22 of the humeral prosthesis and a fixed point on the stem 10 is more appropriate. To meet this requirement, the intermediate connecting member 24b of FIG. 4 is used. In this design, a portion of the intermediate connecting member 24b between the two tapers 50 and 52 is available in a number of incrementally different sizes to allow the surgeon to select the appropriate separation or "neck length" 54 between the tapers 50 and 52, and hence the separation between the head 22 and stem 10 of the prosthesis.

Figure 5:
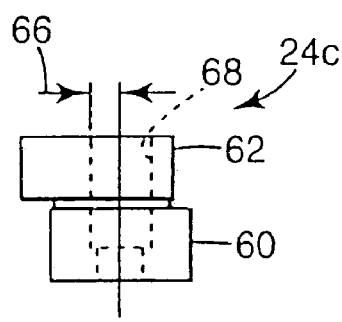

The anterior or posterior offset can be simulated using the design of intermediate connecting member 24c as shown in FIG. 5 to mimic offsets 66 that can naturally occur in the humerus. In this design, the central axes of the first and second male tapers 60 and 62 are parallel and offset from one another as illustrated at 66. The second male taper 62 is counter-bored at an off-center position (e.g., compare bore 68 or FIG. 5 with bores 48 and 58 of FIGS. 3 and 4). This allows the head 22 to be attached on a parallel but not coincident axis to the first male taper 60, and thus to the female taper 30 of the stem 10. Again, this design is available in a number of incrementally different offsets 66 so the surgeon can select the most appropriate intermediate connecting member 24c for each individual patient interoperatively.

Figure 6:
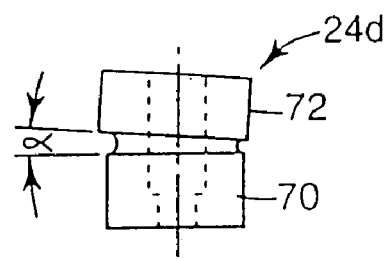

The angle of inclination α of the humeral head relative to the axis of the humeral stem can vary from patient to patient. The intermediate connecting member 24d can simulate this orientation. The design shown in FIG. 6 comprises a portion of the intermediate connecting member 24d that has a generally wedge shaped design. The surgeon will be able to select the wedge-shaped intermediate connecting member 24d from a range of intermediate connecting members 24d having incremental difference in the inclination angle a as shown in FIG. 6, to best fit each individual patient. Due to the wedge-shape, the central axes of the first and second male tapers 70 and 72 of this design are offset from parallel by an angle equal to the inclination angle α.

Any of the features of intermediate connecting members 24a–d illustrated in FIGS. 1 to 6 can be combined to provide the desired variation in neck length 44, 54, 84 anterior or posterior offset 66, 86 or angular inclination a to best suit each individual patient's anatomy.

Figure 7:
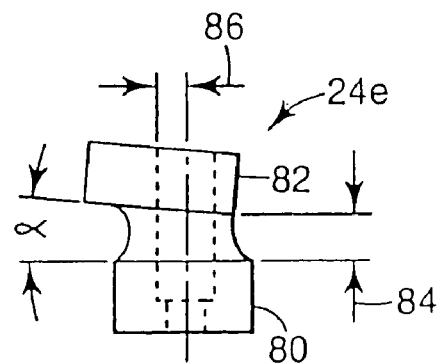

FIG. 7 shows an intermediate connecting member 24e that includes a combination of the angular inclination α as described in FIG. 6, the anterior/posterior offset 86 as depicted in FIG. 5, and the taper separation 84 as illustrated in FIG. 4.

Figure 8:
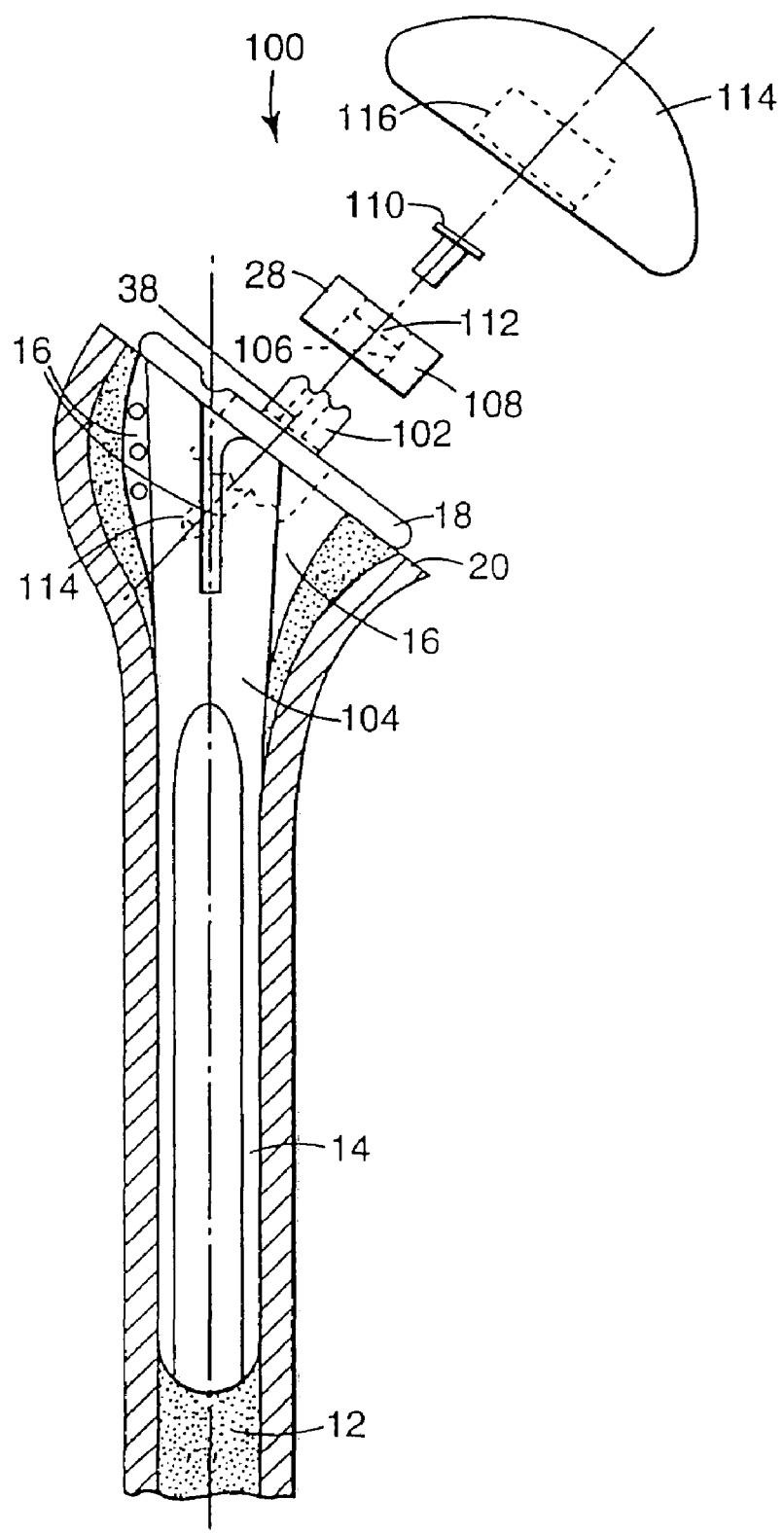
FIG. 8 is an exploded side elevation of a second embodiment of the modular humeral prosthesis according to the invention.

In the above embodiments, the male members of the two connecting surfaces are provided by the intermediate connecting member 24a–e. In an alternative embodiment one or both of the two connecting surfaces provided by the intermediate connecting member may comprise female portions. For example, FIG. 8 illustrates a second embodiment of the modular humeral prosthesis 100 of the invention similar in many respects to the first embodiment shown in FIGS. 17. Differences include the provision of a male tapered connecting portion 102 on the stem 104, and a female tapered connecting portion 106 on the intermediate connecting member 108.

Male connecting portion 102 and female connecting portion 106 are designed for substantially self-locking mating, and preferably have a circular cross section The self-locking function may be accomplished by providing a "Morse taper" on the male and female connecting portions 102 and 106. The female connecting portion 106 constitutes a second embodiment of the first connecting surface of the intermediate connecting member 108.

Optionally, a fastener 110 may be inserted through a bore 112 through the intermediate connecting member 108 and into engagement with a bore 114 in the stem 104 to further secure the female connecting portion 106 of the intermediate connecting member 108 on the stem 104. T Fastener 110 and the bore 114 are provided with interlocking threads. As an alternative embodiment, the male and female connecting portion 102 and 106 could be provided with a non-self-locking configuration; in which case the fastener 110 or another locking mechanism would take on a greater importance.

As is the case with the first embodiment, the head 114 of the second embodiment is provided with a female connecting portion 116, and the second connecting surfaces of the intermediate connecting member 108 comprises a male connecting portion 118. The female and male connecting portions 116 and 118 are also preferably provided with a self-locking tapered configuration, i.e., a Morse taper.

Figure 9:
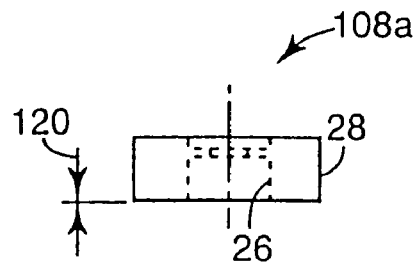
FIGS. 9–13 are various intermediate connecting members according to another embodiment of the invention.
Figure 10:
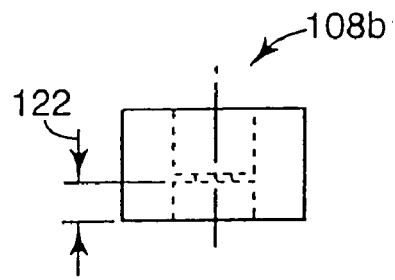

FIGS. 9–13 illustrate various intermediate connecting members 108a—a for use in the prosthesis 100. FIGS. 9 and 10 illustrate two intermediate connecting members 108a and 108b providing two different separations 120 and 122. In this respect, intermediate connecting member 108a is similar to intermediate connecting member 24a of the first embodiment (FIG. 3) due to the minimal separation 120 or 44, and intermediate connecting member 108b is similar to intermediate connecting member 24b of the first embodiment (FIG. 4) due to the greater separation 122 or 54. Both intermediate connecting member 108a and 108b show a zero inclination angle and a zero offset.

Figure 11:
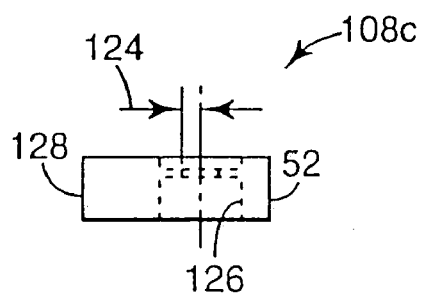

FIG. 11 illustrates another intermediate connecting member 108c having, like member 108a, minimal separation. Intermediate connecting member 108c, however, has a non-zero offset 124. This non-zero offset 124 is accomplished by displacing or offsetting the central axis or axis of rotation of the female locking portion 126 relative to the central axis of axis of rotation of the male locking portion 128 by the offset 124. In this respect, the intermediate connecting member 108c is similar to the intermediate connecting member 24c of the first embodiment (FIG. 5).

Figure 12:
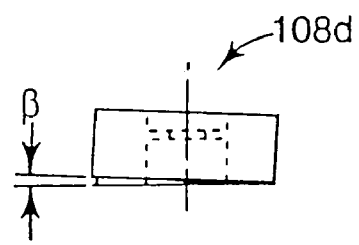

FIG. 12 illustrates yet another intermediate connecting member 108d having, like member 108a, minimal separation and zero offset. Intermediate connecting member 108d, however, has a non-zero inclination angle α. Inclination angle α is similar in function and preferred magnitude to the inclination angle α discussed with respect to the first embodiment (e.g., FIG. 6).

Figure 13:
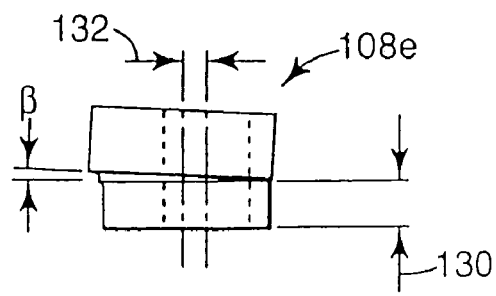

FIG. 13 illustrates an intermediate connecting member 108e having a non-zero separation 130, a non-zero offset 132 and a non-zero inclination angle α. In this respect, intermediate connecting member 108e is similar to intermediate connecting member 24e of the first embodiment (FIG. 7).

Figure 14:
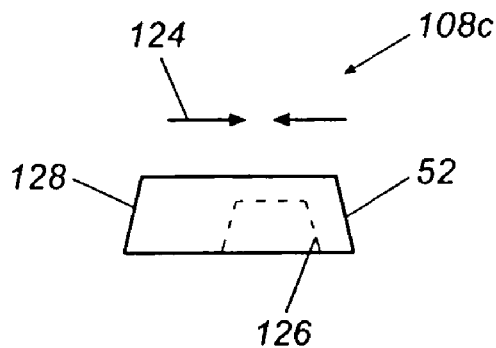
FIGS. 14–16 are various intermediate connecting members according to a further embodiment of the invention.
Figure 15:
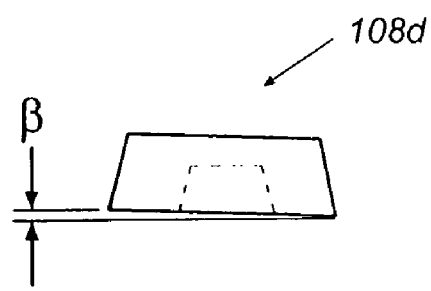
Figure 16:
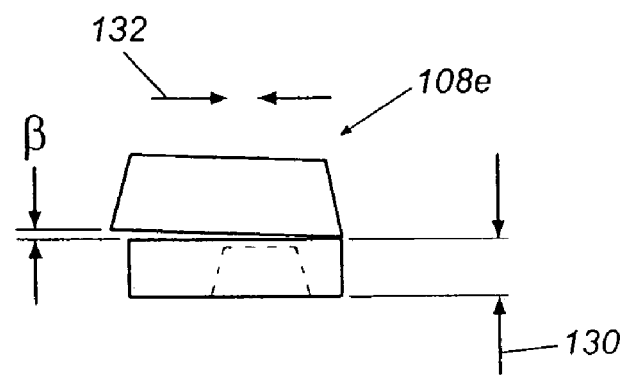

FIGS. 14–16 are various intermediate connecting members corresponding to FIGS. 11–13, but showing the tapered locking portions in more detail.

One consequence of the design of the second embodiment of the prosthesis is that the male connecting portion 118 may have a length extending into the intermediate connecting member, e.g., 108a, a distance sufficient that it is received both in the intermediate connecting member 108a and the void defined by the female connecting portion 116 of the head 114. This is accomplished without any direct engagement between the male connecting portion 118 of the stem 104 and the female connecting portion 116 of the head 114.

Other embodiments, which are not illustrated in the drawing, include (1) the first connecting surfaces comprising a male connecting portion and the second connecting surfaces to comprising a female connecting portion, and (2) both the first and second connecting surfaces comprising female portions.

In summary, at least one advantage of providing an eccentric humeral head along with an intermediate connecting member having an angulation and/or inclination is that although the intermediate connecting member can change the medial offset (offset from glenoid to humeral canal), the eccentric head helps align the humeral head with the glenoid (to account for natural offset in anatomy.) In other words, even though the intermediate connecting member can change the retroversion angle, the humeral head may still not be in center of glenoid. The eccentric head helps provide this alignment. Put another way, the intermediate connecting member provides the ability to adjust the inclination angle and retroversion angle. The addition of eccentric head 200 provides the surgeon with ability to adjust for the posterior offset (i.e., eccentricity) of the humeral head in the plane of the adjusted humeral head.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A modular humeral prosthesis for replacement of the humeral head of a humerus, comprising:
   (a) a stem adapted to be fitted to a resected humerus;
   (b) an eccentric head adapted to approximate the size and shape of a humeral head, having an eccentric mating portion adapted to interface with an intermediate connecting member;
   (c) an intermediate connecting member for connecting the stem to the head, the intermediate connecting member including:
      a first connecting surface that is adapted to cooperate with structure forming part of the stem in order to mount the intermediate connecting member to the stem; and a second connecting surface adapted to cooperate with structure forming part of the head in order to mount the head to the intermediate connecting member, the second connecting surface at least partially nested with the first connecting surface and the first and second surfaces being surfaces of rotation having axes of rotation, the axis of rotation of the first surface non-collinear with the axis of rotation of the second surface.

2. A prosthesis according to claim 1 in which both connecting surfaces are adapted to lock to corresponding structure using a tapered locking mechanism.

3. A prosthesis according to claim 1 in which the second connecting surface is inclined at an angle relative to the first connecting surface.

4. A prosthesis according to claim 1 in which each of the first connecting surface and the second connecting surface has an axis, and in which said axes are offset from each other in order to cause the first connecting surface to be offset from the second connecting surface.

5. A prosthesis according to claim 1 in which (a) the second connecting surface is inclined at an angle relative to the first connecting surface; and (b) the second connecting surface is offset from the first connecting surface.

6. A modular humeral prosthesis according to claim 1 in which the first connecting surface is a female connecting surface and the second connecting surface is a male connecting surface.

7. A modular humeral prosthesis according to claim 1 in which the eccentric head comprises a trench at least partially surrounding the eccentric mating portion.

8. A modular humeral prosthesis for replacement of the humeral head of a humerus, comprising:
  (a) a stem adapted to be fitted to a resected humerus;
  (b) an eccentric head adapted to approximate the size and shape of a humeral head, having an eccentric mating portion adapted to interface with an intermediate connecting member;
  (c) an intermediate connecting member for connecting the stem to the head, the intermediate connecting member including;
    a first connecting surface forming a tapered, generally frustoconically shaped, cavity that is adapted to cooperate with a structure forming part of the stem in order to mount and lock the intermediate connecting member to the stem; and
    a second connecting surface that is generally frustoconically shaped, tapered, and adapted to cooperate with structure forming part of the head in order to mount and lock the head to the intermediate connecting member,
    the second connecting surface at least partially nested with the first connecting surface and the first and second surfaces being surfaces of rotation having axes of rotation, the axis of rotation of the first surface non-collinear with the axis of rotation of the second surface.

9. A prosthesis according to claim 8 in which the second connecting surface is inclined at an angle relative to the first connecting surface.

10. A prosthesis according to claim 8 in which each of the first connecting surface and the second connecting surface has an axis, and in which said axes are offset from each other in order to cause the first connecting surface to be offset from the second connecting surface.

11. A prosthesis according to claim 8 in which (a) the second connecting surface is inclined at an angle relative to the first connecting surface; and (b) the second connecting surface is offset from the first connecting surface.

12. A modular humeral prosthesis according to claim 8 in which the first connecting surface is a female connecting surface and the second connecting surface is a male connecting surface.

13. A modular humeral prosthesis according to claim 8 in which the eccentric head comprises a trench at least partially surrounding the eccentric mating portion.

14. A method of replacing a humeral head in a patient, comprising:
  (a) resecting the proximal end of the humerus to remove the head and expose the medullary canal of the humerus;
  (b) inserting a stem of a prosthesis into the medullary canal of the resected humerus, the prosthesis comprising:
    (i) the stem;
    (ii) an eccentric head adapted to approximate the size and shape of a humeral head, having an eccentric mating portion adapted to interface with an intermediate connecting member;
    (iii) one of a plurality of intermediate connecting members for connecting the stem to the head, each intermediate connecting member including:
      a first connector formed as a surface of rotation and adapted to cooperate with the stem in order to mount the intermediate connecting member to the stem,
      a second connector formed as a surface of rotation and adapted to cooperate with the head in order to mount the head to the intermediate connecting member, the second connector surface at least partially nested with the first connector surface,
    the plurality of intermediate connecting members including at least some members having different angles of inclination between their first and second connectors;
  (c) selecting a particular intermediate connecting member to provide a desired angle of inclination of the head relative to the humerus; and
  (d) mounting the intermediate connecting member to the stem, mounting the intermediate connecting member to the head, the mounting of the intermediate connecting member to the stem and head imparting the desired angle of inclination of the head relative to the humerus.

15. A method according to claim 14 in which the eccentric head comprises a trench at least partially surrounding the eccentric mating portion.

16. A method of replacing a humeral head in a patient, comprising:
  (a) resecting the proximal end of the humerus to remove the head and expose the medullary canal of the humerus;
  (b) inserting a stem of a prosthesis into the medullary canal of to resected humerus, the prosthesis comprising:
    (i) the stem;
    (ii) an eccentric head adapted to approximate the size and shape of a humeral head, having an eccentric mating portion adapted to interface with an intermediate connecting member;
    (iii) one of a plurality of intermediate connecting members for connecting the stem to the head, each intermediate connecting member including:

a first connector formed as a surface of rotation and adapted to cooperate with the stem in order to mount the intermediate connecting member to the stem, a second connector formed as a surface of rotation and adapted to cooperate with the head in order to mount the head to the intermediate connecting member, the second connector surface at least partially nested with the first connector surface, the plurality of intermediate connecting members including at least some members with each of the first connector and second connector having an axis, and in which said axes are offset from each other in order to cause the first connector to be offset from the second connector, (c) selecting a particular intermediate connecting member to provide a desired offset of the head relative to the stem; and (d) mounting the intermediate connecting member to the stem, mounting the intermediate connecting member to the head, the mounting of the intermediate connecting member to the stem and head imparting the desired offset of the head relative to the humerus.

17. A method according to claim 16 in which the eccentric head comprises a trench at least partially surrounding the eccentric mating portion.

* * * * *